(12) United States Patent
Jackman

(10) Patent No.: US 6,686,501 B2
(45) Date of Patent: Feb. 3, 2004

(54) PROCESSES FOR PREPARING 3,3-DIMETHYLBUTYRIC ACID

(75) Inventor: Dennis E. Jackman, Prairie Village, KS (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 10/068,631

(22) Filed: Feb. 5, 2002

(65) Prior Publication Data

US 2003/0149302 A1 Aug. 7, 2003

(51) Int. Cl.$^7$ .......................... C07C 53/00; C07B 53/00
(52) U.S. Cl. .................................. 562/606; 562/512
(58) Field of Search ......................... 562/606, 512

(56) References Cited

U.S. PATENT DOCUMENTS 2,004,066 A * 6/1935 Whitmore ............... 562/606
3,956,411 A * 5/1976 Mahan et al. ............ 570/237
4,536,594 A * 8/1985 Deschamps et al. ...... 562/400
5,907,060 A * 5/1999 Stelzer ..................... 562/606

FOREIGN PATENT DOCUMENTS

JP         0813775    * 2/1996

* cited by examiner

Primary Examiner—Alan L. Rotman
Assistant Examiner—Taylor V Oh
(74) Attorney, Agent, or Firm—Richard E.L. Henderson; Joseph C. Gil

(57) ABSTRACT

A process for preparing 3,3-dimethylbutyric acid includes the steps of reacting trimethylpyruvic acid with a first portion of hydrazine to obtain a ketazine, and treating the ketazine with base and a second portion of hydrazine.

20 Claims, No Drawings

PROCESSES FOR PREPARING 3,3-DIMETHYLBUTYRIC ACID

FIELD OF THE INVENTION

This invention relates to processes for preparing 3,3-dimethylbutyric acid. More particularly, this invention relates to processes for preparing 3,3-dimethylbutyric acid by reacting trimethylpyruvic acid with hydrazine to obtain an intermediate, and treating the intermediate with hydrazine and base. This invention also relates to processes for preparing a ketazine of trimethylpyruvic acid.

BACKGROUND OF THE INVENTION 3,3-Dimethylbutyric acid (DMBA), also called 3,3-dimethylbutanoic acid or tert-butylacetic acid, may be used as an intermediate in the synthesis of other chemical compounds, such as pharmaceutical chemicals or agricultural chemicals. The ketazine prepared using trimethylpyruvic acid (TMPA), also called 3,3-dimethyl-2-oxobutyric acid, may also be used as an intermediate in the synthesis of other chemical compounds. Agricultural chemicals include insecticidally, fungicidally and/or herbicidally active compounds.

3,3-Dimethylbutyric acid may be prepared by reacting tert-butanol or tert-butyl chloride with vinylidene chloride in the presence of sulfuric acid and $BF_3$.

Stelzer, U.S. Pat. No. 5,907,060, discloses a process for preparing 3,3-dimethylbutyric acid by reacting trimethylpyruvic acid with hydrazine hydrate to obtain a hydrazone, and subsequently treating the hydrazone with a base.

Unfortunately, $BF_3$ can be difficult to handle. Additionally, prior art processes for preparing 3,3-dimethylbutyric acid may result in 3,3-dimethylbutyric acid which is contaminated with other organic acids which must be removed by solvent extraction and recovery from the solvent. For example, commercially available TMPA typically contains about 10%, by weight, pivalic acid and from about 0 to about 5%, by weight, 2-hydroxy-3,3-dimethylbutyric acid, and thus in many prior art processes using TMPA the resulting DMBA contains comparable levels of pivalic acid and, 2-hydroxy-3,3-dimethylbutyric acid.

Thus there is a need for methods of preparing 3,3-dimethylbutyric acid wherein the level of other organic acids in the product is decreased. There is also a need for methods of preparing 3,3-dimethylbutyric acid which do not require the use of $BF_3$.

SUMMARY OF THE INVENTION

Accordingly, it is an object of the present invention to obviate problems of the prior art.

It is also an object of the present invention to provide methods of preparing 3,3-dimethylbutyric acid wherein the level of other organic acids in the product are decreased.

It is a further object of the present invention to provide methods of preparing 3,3-dimethylbutyric acid which do not require the use of $BF_3$.

These and additional objects are provided by the processes of the invention. In one embodiment, the invention is directed to processes for preparing 3,3-dimethylbutyric acid comprising the steps of reacting trimethylpyruvic acid with a first portion of hydrazine to obtain a ketazine, and treating the ketazine with base and a second portion of hydrazine.

In another embodiment, the invention is directed to processes for preparing 3,3-dimethylbutyric acid comprising the steps of reacting trimethylpyruvic acid with hydrazine to obtain a ketazine, isolating the ketazine, and treating the ketazine with hydrazine and base.

In a further embodiment, the invention is directed to processes for preparing 3,3-dimethylbutyric acid comprising the steps of treating a composition comprising water and trimethylpyruvic acid with hydrazine to obtain an intermediate, wherein less than one mole of hydrazine is used per mole of trimethylpyruvic acid, and treating the intermediate with hydrazine and base.

In yet another embodiment, the invention is directed to processes a ketazine comprising the step of reacting trimethylpyruvic acid with hydrazine to obtain the ketazine.

The processes of the invention of the invention are advantageous in that the 3,3-dimethylbutyric acid may be prepared in the absence of $BF_3$.

Processes in accordance with the invention may be used to prepare 3,3-dimethylbutyric acid without producing large amounts of other organic acids. Thus, processes in accordance with the present invention avoid the need for additional steps directed to removal of other organic acids.

Further, as the ketazine intermediate may be isolated and dried prior to treatment with hydrazine and base, processes in accordance with the present invention do not require large amounts of water be removed.

These and additional aspects, objects and advantages of the invention are more fully described in the following detailed description.

DETAILED DESCRIPTION

The present invention is directed to process from preparing 3,3-dimethylbutyric acid and the ketazine of trimethylpyruvic acid.

As used herein, "hydrazine " is intended to refer to anhydrous hydrazine, hydrazine hydrate, hydrazine hydrochloride, hydrazine sulfate and hydrazine tartrate. Preferably the hydrazine is hydrazine hydrate.

In one embodiment of the invention, a ketazine is prepared by reacting trimethylpyruvic acid (TMPA) with hydrazine, while in another embodiment of the invention, 3,3-dimethylbutyric acid (DMBA) is prepared by reacting trimethylpyruvic acid with hydrazine to obtain a ketazine and subsequently treating the ketazine with base and hydrazine.

In one embodiment of the invention, 3,3-dimethylbutyric acid (DMBA) is prepared by reacting trimethylpyruvic acid with hydrazine to obtain a ketazine, isolating the ketazine, and subsequently treating the ketazine with base and hydrazine. Hydrazines such a hydrazine hydrate contain water, and TMPA may be in the form of an aqueous composition comprising water and a TMPA salt, thus the TMPA and hydrazine reaction mixture may include water. The isolation of the ketazine prior to treatment with base and additional hydrazine removes the organic impurities and a large amount of water that would otherwise have to be removed from the final DBMA product. Some water is typically present or formed during the treatment of the ketazine with the base and additional hydrazine to obtain the DMBA, but the amount of water to be removed from the final DBMA product is reduced by the step of isolating the ketazine prior to the treatment with base. Thus, in contrast with many prior art processes, processes in accordance with the present invention wherein the ketazine is isolated before treatment with base and hydrazine do not require the removal of large amounts of water from the final DBMA product.

While not being bound by theory, the process of preparing the DMBA is believed to occur as set forth below:

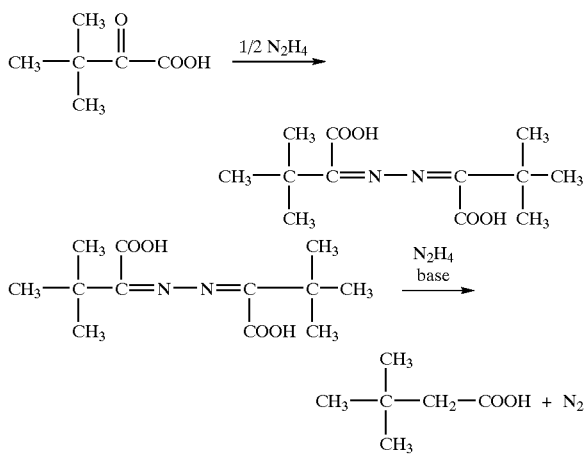

The TMPA may be free of water, or may be in the form of an aqueous composition comprising water and a TMPA salt. Suitable TMPA salts include alkali metal salts, such as TMPA sodium salt. In one embodiment the TMAP is in the form of an aqueous composition comprising from about 7% to about 8%, by weight, TMPA sodium salt.

"Free TMPA", that is, TMPA which is not in the form of a salt, may be obtained by adding an acid, typically an inorganic acid, in order to convert the TMPA salt, such as TMPA sodium salt, to free TMPA. Suitable acids include HCl, $H_2SO_4$, and $H_3PO_4$. If free TMPA rather than TMPA salt is used in the process, no acid is required.

The process of preparing the ketazine of TMPA (TMPA ketazine) includes the step of treating TMPA with hydrazine, preferably hydrazine hydrate. Typically one mole of TMPA is reacted with less than one mole of hydrazine. In one embodiment of the invention the molar ratio of TMPA to hydrazine is from about 1:0.5 to about 1:1, preferably from about 1:0.5 to about 1:0.8, more preferably about 1:0.5 to about 1:07, even more preferably about 1:0.5. In other embodiments the molar ratio of TMPA to hydrazine is from about 1:0.6 to about 1:1, from about 1:0.8 to about 1:1, or from about 1:0.6 to about 1:0.7.

Generally the step of preparing the TMPA ketazine occurs at a pH of from about 0.1 to about 3. In embodiments of the invention the step of preparing the TMPA ketazine may occur at a pH of from about 0.1 to about 1, or from about 0.5 to about 3. The pH of the aqueous composition may be adjusted with any suitable acid or base. Suitable acids include HCl, $H_2SO_4$, and $H_3PO_4$, while suitable bases include NaOH and KOH. In one embodiment of the invention the aqueous composition comprises water, TMPA and an acid, preferably HCl.

The step of reacting the TMPA and the hydrazine is performed for a time and at a temperature and pressure sufficient for the TMPA ketazine to be formed. Generally the step of preparing the TMPA ketazine occurs at a temperature of from about 0° C. to about 80° C., preferably from about 20° C. to about 60° C., and at a pressure of from about 100 to about 900, preferably from about 600 to about 800, mg Hg. The reaction composition comprising the TMPA, water, hydrazine, and any optional solvent and/or pH adjuster is generally allowed to stand for at least about 1 hour, preferably at least about 2 hours, before filtering to obtain the solids comprising TMPA ketazine. In one embodiment the reaction composition is allowed to stand from about 1 to about 10, preferably from about 3 to about 6, hours before filtering to obtain the solids comprising TMPA ketazine. The solids may be washed with a small amount of water before drying.

The (TMPA ketazine) may be used to prepare DMBA by treating the TMPA ketazine with base and a hydrazine, preferably hydrazine hydrate. The product obtained after treating the TMPA ketazine with hydrazine and base comprises the DMBA. Generally the product comprises no more than about 1%, preferably no more than about 0.5%, by weight, of organic acids other than DMBA.

Typically at least about one mole of base is used per mole of TMPA ketazine. In one embodiment of the invention the molar ratio of TMPA ketazine to base is from about 1:1 to about 1:10, preferably from about 1:2 to about 1:6, more preferably about 1:4. Typically at least about one mole of hydrazine is used per mole of TMPA ketazine. In one embodiment of the invention the molar ratio of TMPA ketazine to hydrazine is from about 1:1 to about 1:8, preferably from about 1:2 to about 1:6, more preferably about 1:3.

Suitable bases include alkali metal hydroxides, such as sodium hydroxide and potassium hydroxide; alkali metal alkoxides, such as sodium methoxide, sodium ethoxide and potassium tert-butoxide; and combinations thereof. In one embodiment the base is selected from the group consisting of potassium hydroxide, sodium hydroxide and mixtures thereof. Generally the step of preparing the DMBA occurs at a pH of from about 10 to about 14, preferably from about 12 to about 14.

The treatment of the ketazine with hydrazine and base generally occurs in the presence of an organic base. Suitable solvents include alcohols, such as diglycol and triglycol (triethylene glycol), methanol, ethanol, n- or i-propanol, n-, l-, sec- or tert-butanol, octanol, hexanol, ethanediol, propane-1,2-diol, ethoxyethanol, methoxyethanol, diethylene glycol monomethyl ether, diethylene glycol monoethyl ether; sulfoxides, such as dimethyl sulfoxide; ether solvents, such as diethylene glycol dimethyl ether (diglyme) and diethylene glycol diethyl ether; and combinations thereof. Preferably the solvent is selected from the group consisting of butanol, pentanol, hexanol and combinations thereof, more preferably the solvent is butanol.

The step of treating the TMPA ketazine with base and hydrazine is performed for a time and at a temperature and pressure sufficient for the DMBA to be formed. Generally the step of preparing the DMBA occurs at a temperature of from about 105° C. to about 130°C., preferably from about 116° C. to about 117° C., and at a pressure of from about 600 to about 1000, preferably from about 700 to about 800, mg Hg.

After heating at the desired temperature and for the desired time, the reaction mixture comprising DMBA, solvent, and any unreacted hydrazine, ketazine and base is cooled, and the DMBA is isolated. Generally the DMBA in the reaction mixture is in the form of a salt, the reaction mixture may be acidified to obtain free DMBA.

The DMBA may be isolated using any suitable technique. For example, in one embodiment crystallized DMBA salt is collected from the cooled reaction mixture. In another embodiment steam distillation of the butanol followed by cooling or evaporation to collect the DMBA salt, or acidification to obtain DMBA.

In accordance with one embodiment of the invention, after heating for a suitable time and temperature, the resulting composition comprising the DMBA, solvent and any remaining hydrazine and/or base may be cooled. Water may be added and the solvent azeotroped and removed. The water layer may be mixed with a different solvent, such as a solvent selected from the group consisting of aromatic solvents, hydrocarbon solvents, chlorinated hydrocarbon solvents and ketones, preferably toluene and methyl isobutyl ketone, and acidified to a pH of less than about 3, preferably less than about 2. The layers may be separated, and the DMBA isolated from the toluene layer.

In one embodiment of the invention the process of preparing 3,3-dimethylbutyric acid from trimethylpyruvic acid uses no more than about 5, preferably from about 4 to about 1, more preferably from about 3 to about 1, total moles of hydrazine per mole of trimethylpyruvic acid. As used herein "total moles of hydrazine" is intended to refer to the total of the hydrazine used to prepare the TMPA ketazine, and the hydrazine used to prepare DMBA from the TMPA ketazine.

In one preferred embodiment of the invention the process of preparing 3,3-dimethylbutyric acid occurs in the absence of $BF_3$.

Methods in accordance with the invention may be used to prepare a product with low levels of organic acids other than the DMBA. In one embodiment of the invention the product comprising the DMBA comprises no more than about 0.5% to about 1%, by weight, of organic acids other than DMBA.

Throughout the examples and the present specification, parts and percentages are by weight unless otherwise specified. The following example is illustrative only and is not intended to limit the scope of the processes of the invention as defined by the claims.

EXAMPLES

Example A.

The ketazine of trimethylpyruvic acid (TMPA) is prepared by placing 271 grams of 62% (1.77 moles) TMPA in 2 liters of water and adding 20 mls of concentrated HCl and 50 grams of (1 mole) hydrazine hydrate with stirring. The HCl is used to ensure that no TMPA sodium salt is present. The solution is allowed to stand for at least about 5 hours and is filtered. The solids may be washed with a small amount of water before drying. The ketazine (201 grams) is a white powder. The yield is 89%.

Example B.

A reactor is charged with a mixture of 100 ml of butanol, 42.5 grams (0.116 moles) of the ketazine of TMPA, 25 grams (0.5 moles) of hydrazine hydrate and 27 grams of 100% (0.667 moles) sodium hydroxide. The mixture is slowly heated to reflux and azeotrope water until the temperature reaches about 116–117° C. The temperature is maintained at about 116–117° C. for from about 3 to about 4 hours. About 13 grams of water is azeotroped and removed. In contrast, prior art methods typically produce larger amounts of water which must be azeotroped and removed.

After the heating is finished, 200 ml of water is added. Butanol is azeotroped and removed, and the water layer is returned to the reactor. Toluene (75 mls) is added and the resulting composition is acidified to a pH of less than about 2 while the temperature is maintained at less than about 40° C. The layers are separated, and the toluene layer is analyzed. The solvent free analysis of the toluene layer is 0.5% pivalic acid and 99% 3,3-dimethylbutyric acid (DMBA). The DMBA yield is 94%.

Additional embodiments and modifications within the scope of the claimed invention will be apparent to one of ordinary skill in the art. Accordingly, the scope of the present invention shall be considered in terms of the following claims, and is understood not to be limited to the details of the processes described in the specification.

What is claimed is:

1. A process for preparing 3,3-dimethylbutyric acid comprising the steps of:
    (a) reacting trimethylpyruvic acid with a first portion of hydrazine to obtain a ketazine, and
    (b) treating the ketazine with base and a second portion of hydrazine.

2. A process according to claim 1, wherein the hydrazine is in the form of hydrazine hydrate.

3. A process according to claim 1, wherein the trimethylpyruvic acid is present in the form of a composition comprising trimethylpyruvic acid and water.

4. A process according to claim 1, wherein less than one mole of hydrazine is used per mole of trimethylpyruvic acid in step of reacting trimethylpyruvic acid with the first portion of hydrazine.

5. A process according to claim 1, wherein the molar ratio of trimethylpyruvic acid to the first portion of hydrazine is from about 1:0.5 to about 1:0.6.

6. A process according to claim 1, wherein the molar ratio of trimethylpyruvic acid to the first portion of hydrazine is about 1:0.5.

7. A process according to claim 1, wherein the molar ratio of ketazine to base is from about 1:2 to about 1:6.

8. A process for preparing 3,3-dimethylbutyric acid comprising the steps of:
    (a) reacting trimethylpyruvic acid with hydrazine to obtain a ketazine,
    (b) isolating the ketazine, and
    (c) treating the ketazine with hydrazine and base.

9. A process according to claim 8, wherein the step of reacting trimethylpyruvic acid with hydrazine comprises adding hydrazine to a composition comprising water and trimethylpyruvic acid.

10. A process according to claim 8, wherein the molar ratio of trimethylpyruvic acid to hydrazine in step (a) is from about 1:0.5 to about 1:0.6.

11. A process according to claim 8, wherein the molar ratio of ketazine to base in step (b) is from about 1:2 to about 1:6.

12. A process according to claim 8, wherein the molar ratio of ketazine to hydrazine in step (b) is from about 1:1 to about 1:8.

13. A process according to claim 8, wherein the step of treating the ketazine with hydrazine and base comprises the steps of:
    (i) mixing the ketazine with hydrazine hydrate, base and a solvent selected from the group consisting of alcohols, sulfoxides, ethers, and combinations thereof to obtain a mixture, and
    (ii) heating the mixture at a temperature of from about 114° C. to about 120° C., for a time of from about 2 hours to about 8 hours.

14. A process according to claim 13, further comprising the step of isolating the 3,3-dimethylbutyric acid.

15. A process for preparing 3,3-dimethylbutyric acid comprising the steps of:
    (a) treating a composition comprising water and trimethylpyruvic acid with hydrazine hydrate to obtain ketazine wherein less than one mole of hydrazine hydrate is used per mole of trimethylpyruvic acid, and
    (b) treating the ketazine with hydrazine hydrate and base.

16. A process according to claim 15, wherein the molar ratio of trimethylpyruvic acid to hydrazine hydrate is from about 1:0.5 to about 1:0.6.

17. A process according to claim 15, wherein the molar ratio of intermediate to hydrazine hydrate is from about 1:1 to about 1:5, and the molar ratio of the ketazine to base is from about 1:2 to about 1:6.

18. A process for preparing a ketazine comprising the step of reacting trimethylpyruvic acid with hydrazine to obtain the ketazine.

19. A process according to claim 18, wherein the hydrazine is hydrazine hydrate and the molar ratio of trimethylpyruvic acid to hydrazine hydrate is from about 1:0.5 to about 1:0.6.

20. A process according to claim 19, wherein the step of reacting trimethylpyruvic acid with hydrazine hydrate comprises adding the hydrazine hydrate and an acid to a composition comprising trimethylpyruvic acid and water.

* * * * *